(12) United States Patent
Rekers

(10) Patent No.: US 8,378,154 B2
(45) Date of Patent: Feb. 19, 2013

(54) PROCESS FOR THE PREPARATION OF ALKYLENE GLYCOL

(75) Inventor: Dominicus Maria Rekers, Amsterdam (NL)

(73) Assignee: Shell Oil Company, Houston, TX (US)

(*) Notice: Subject to any disclaimer, the term of this patent is extended or adjusted under 35 U.S.C. 154(b) by 212 days.

(21) Appl. No.: 12/936,705

(22) PCT Filed: Apr. 8, 2009

(86) PCT No.: PCT/EP2009/054269
§ 371 (c)(1),
(2), (4) Date: Nov. 2, 2010

(87) PCT Pub. No.: WO2009/124987
PCT Pub. Date: Oct. 15, 2009

(65) Prior Publication Data
US 2011/0054224 A1 Mar. 3, 2011

(30) Foreign Application Priority Data

Apr. 9, 2008 (EP) .................................. 08103452

(51) Int. Cl.
*C07C 29/159* (2006.01)
*C07C 27/04* (2006.01)
(52) U.S. Cl. ..................................................... 568/867
(58) Field of Classification Search ............. 568/867
See application file for complete search history.

(56) References Cited

U.S. PATENT DOCUMENTS

| | | | |
|---|---|---|---|
| 4,400,559 A | 8/1983 | Bhise | 568/858 |
| 4,822,926 A | 4/1989 | Dye | 568/867 |
| 4,831,196 A | 5/1989 | Buonicore et al. | 568/867 |
| 5,218,135 A | 6/1993 | Buysch et al. | 558/277 |
| 5,763,691 A * | 6/1998 | Kawabe et al. | 568/867 |
| 6,080,897 A | 6/2000 | Kawabe | 568/858 |
| 6,417,411 B2 | 7/2002 | Kakimoto et al. | 568/867 |
| 8,063,256 B2 * | 11/2011 | Van Kruchten | 568/910 |
| 2003/0098281 A1 | 5/2003 | Shutt et al. | 210/663 |
| 2004/0175316 A1 | 9/2004 | Bos et al. | 423/245.1 |
| 2008/0182999 A1 | 7/2008 | Rekers et al. | 549/512 |
| 2009/0143627 A1 * | 6/2009 | Van Kruchten et al. | 568/860 |

FOREIGN PATENT DOCUMENTS

| | | |
|---|---|---|
| CN | 1699359 | 11/2005 |
| EP | 24628 | 12/1980 |
| EP | 776890 | 6/1997 |
| GB | 2107712 | 5/1983 |
| JP | 56-40625 | 4/1981 |

* cited by examiner

*Primary Examiner* — Brian J Davis

(57) ABSTRACT

The invention provides a process for the preparation of an alkylene glycol from an alkene wherein conversion of alkylene oxide to alkylene glycol occurs in an alkylene oxide absorber and optionally in further reactors, and alkylene glycol is extracted from fat absorbent by contacting the fat absorbent with a lean solvent, thereby producing fat solvent, recovering alkylene glycol from the fat solvent and recycling the lean solvent.

9 Claims, 2 Drawing Sheets

PROCESS FOR THE PREPARATION OF ALKYLENE GLYCOL

PRIORITY CLAIM

The present application claims priority to European Patent Application 08103452.2 filed 9 Apr. 2008.

FIELD OF THE INVENTION

The present invention relates to a process for the preparation of an alkylene glycol from an alkene.

BACKGROUND OF THE INVENTION

Monoethylene glycol is used as a raw material in the manufacture of polyester fibres, polyethylene terephthalate (PET) plastics and resins. It is also incorporated into automobile antifreeze liquids.

Monoethylene glycol is typically prepared from ethylene oxide, which is in turn prepared from ethylene. Ethylene and oxygen are passed over a silver oxide catalyst, typically at pressures of 10-30 bar and temperatures of 200-300° C., producing a product stream comprising ethylene oxide, carbon dioxide, ethylene, oxygen and water. The amount of ethylene oxide in the product stream is usually between about 0.5 and 10 weight percent. The product stream is supplied to an ethylene oxide absorber and the ethylene oxide is absorbed by a recirculating solvent stream containing mostly water. The ethylene oxide-depleted stream is partially or entirely supplied to a carbon dioxide absorption column wherein the carbon dioxide is at least partially absorbed by a recirculating absorbent stream. Gases that are not absorbed by the recirculating absorbent stream are recombined with any gases bypassing the carbon dioxide absorption column and are recycled to the ethylene oxide reactor.

The solvent stream leaving the ethylene oxide absorber is referred to as fat absorbent. The fat absorbent is supplied to an ethylene oxide stripper, wherein ethylene oxide is removed from the fat absorbent as a vapour stream. The ethylene oxide-depleted solvent stream is referred to as lean absorbent and is recirculated to the ethylene oxide absorber to absorb further ethylene oxide.

The ethylene oxide obtained from the ethylene oxide stripper can be purified for storage and sale or can be further reacted to provide ethylene glycol. In one well-known process, ethylene oxide is reacted with a large excess of water in a non-catalytic process. This reaction typically produces a glycol product stream consisting of almost 90 weight percent monoethylene glycol, the remainder being predominantly diethylene glycol, some triethylene glycol and a small amount of higher homologues. In another well-known process, ethylene oxide is reacted with an equimolar amount or slight excess of water in the presence of a hydrolysis catalyst. In another well-known process, ethylene oxide is catalytically reacted with carbon dioxide to produce ethylene carbonate. The ethylene carbonate is subsequently hydrolysed to provide ethylene glycol. Reaction via ethylene carbonate can improve the selectivity to monoethylene glycol.

Most conventional processes comprise steps of converting ethylene to ethylene oxide, absorbing ethylene oxide from a gas stream into a liquid stream and subsequently reacting ethylene oxide to ethylene glycol. GB 2 107 712 describes a process wherein the absorption and reaction steps are combined: gases from the ethylene oxide reactor are supplied directly to a reactor wherein ethylene oxide is converted to ethylene carbonate or to a mixture of ethylene glycol and ethylene carbonate.

The ethylene glycol-containing solutions that result in the known processes are subjected to water removal, typically in a series of flashing and/or distillation steps. The water removal can be an energy intensive process, particularly if a large excess of water is present in the ethylene glycol-containing solution. Processes wherein the absorption and reaction steps are combined provide ethylene glycol product solutions containing particularly high quantities of water, so the water removal will necessitate significant energy usage.

The present inventors have sought to further improve the manufacture of alkylene glycol from an alkene. In particular, the present inventors have sought to provide a process that reduces the capital costs and/or the running costs of a plant, whilst ensuring high selectivity.

SUMMARY OF THE INVENTION

Accordingly, the present invention provides a process for the preparation of an alkylene glycol from an alkene comprising steps of:

(a) reacting the alkene with oxygen in the presence of a catalyst in a reactor to produce a gas composition comprising alkylene oxide, alkene, oxygen, carbon dioxide and water vapour;

(b) supplying the gas composition from (a) to an alkylene oxide absorber, supplying lean absorbent to the alkylene oxide absorber, contacting the gas composition with lean absorbent in the absorber in the presence of one or more catalysts that promote hydrolysis and withdrawing fat absorbent from the absorber;

(c) optionally supplying the fat absorbent to one or more reactor vessels;

wherein conversion of alkylene oxide to alkylene glycol occurs in step (b) and optionally in step (c), such that the fat absorbent resulting from step (b) or step (c) comprises alkylene glycol; and further comprising steps of:

(d) contacting the fat absorbent from step (b) or step (c) with a lean solvent, thereby extracting alkylene glycol from the fat absorbent and producing fat solvent; and (e) recovering alkylene glycol from the fat solvent, thereby producing lean solvent, and recycling the lean solvent to step (d).

The process of the present invention combines absorption and reaction steps such that alkylene glycol is produced in the alkylene oxide absorber, providing an alkylene glycol product solution in a process that uses fewer or smaller reaction vessels than the conventional process, and additionally uses liquid-liquid extraction to avoid the energy costs associated with conventional removal of the significant quantities of water in the product solution. JP 56-40625 discloses a method for extraction of polyols such as ethylene glycol from aqueous solutions, wherein a hydrocarbon or chlorohydrocarbon solvent is used to extract the polyol, but does not address how the ethylene glycol solution may be prepared. The present inventors have devised a process wherein liquid-liquid extraction is advantageously employed in combination with a process for preparing an alkylene glycol from an alkene wherein absorption and reaction both occur in the alkylene oxide reactor.

DETAILED DESCRIPTION OF THE INVENTION

Figure 1:
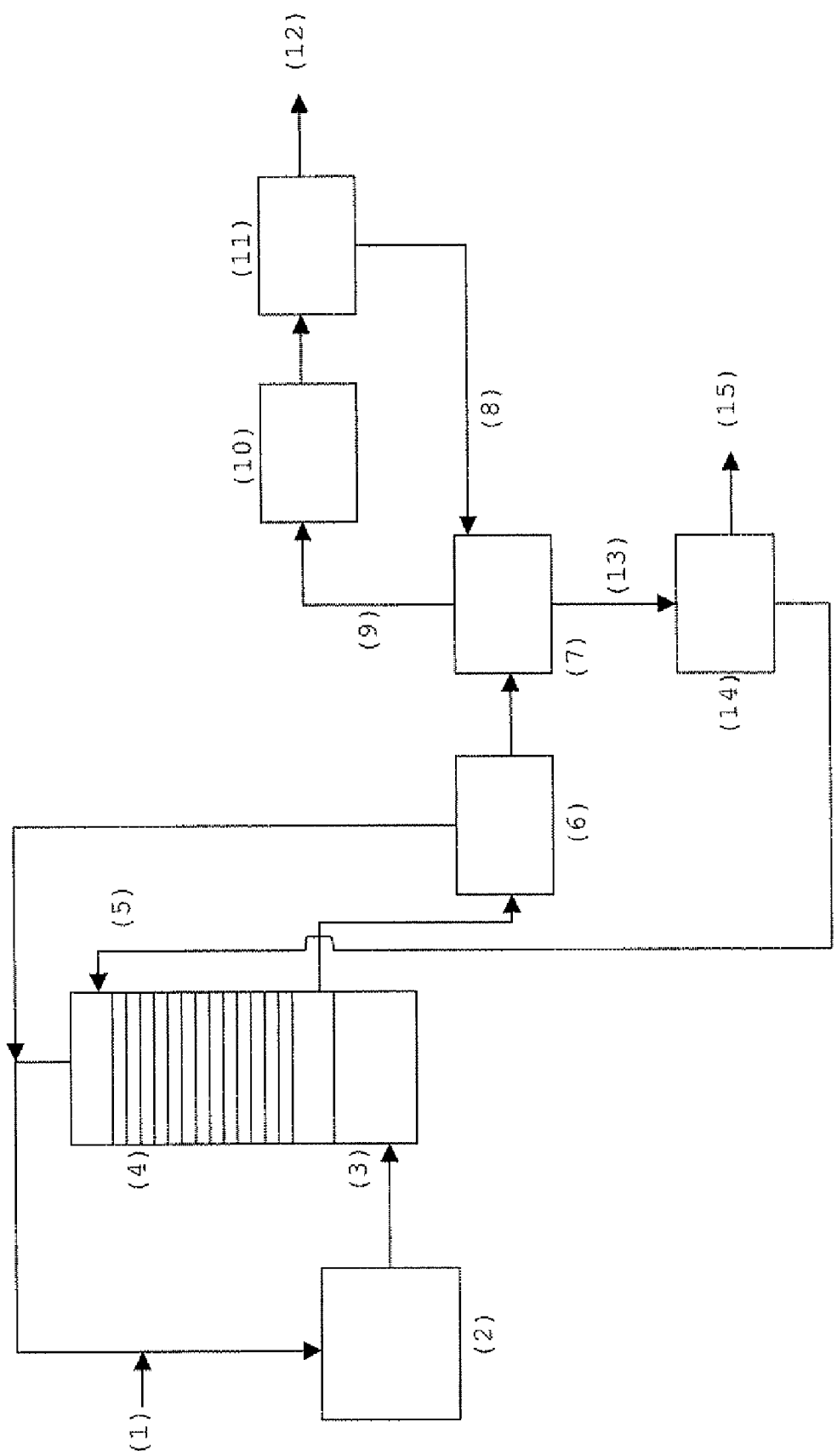
FIG. 1 is a schematic diagram showing a process according to a first embodiment of the invention.

The present invention provides a process for the preparation of an alkylene glycol from an alkene:

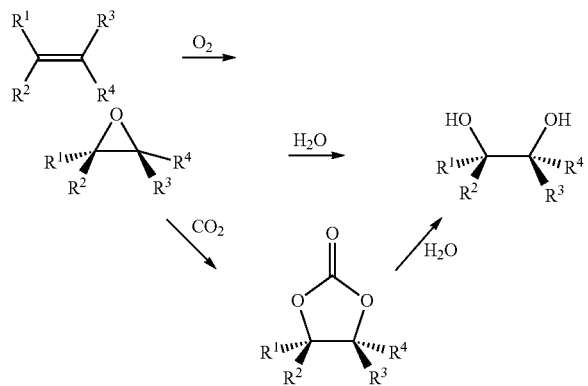

$R^1$, $R^2$, $R^3$ and $R^4$ are preferably chosen from hydrogen or an optionally substituted alkyl group having from 1 to 6 carbon atoms, more preferably from 1 to 3 carbon atoms. As substituents, moieties such as hydroxy groups may be present. Preferably, $R^1$, $R^2$ and $R^3$ represent hydrogen atoms and $R^4$ represents hydrogen or a non-substituted $C_1$-$C_3$-alkyl group and, more preferably, $R^1$, $R^2$, $R^3$ and $R^4$ all represent hydrogen atoms.

Examples of suitable alkenes therefore include ethylene and propylene. In the present invention the most preferred alkene is ethylene.

The alkene is reacted with oxygen in the presence of a catalyst in a reactor to produce a gas composition comprising alkylene oxide, alkene, oxygen, carbon dioxide and water vapour. The oxygen may be supplied as oxygen or as air, but is preferably supplied as oxygen. Ballast gas, for example methane or nitrogen, is typically supplied to allow operation at high oxygen levels without causing a flammable mixture. Moderator, e.g. monochloroethane or dichloroethane, may be supplied for ethylene oxide catalyst performance control. The alkene, oxygen, ballast gas and moderator are preferably supplied to recycle gas that is supplied to the alkylene oxide reactor from the alkylene oxide absorber.

The alkylene oxide reactor is typically a multitubular, fixed bed reactor. The catalyst is preferably finely dispersed silver and optionally promoter metals on a support material, for example, alumina. The reaction is preferably carried out at pressures of greater than 1 MPa and less than 3 MPa and temperatures of greater than 200° C. and less than 300° C. The gas composition from the alkylene oxide reactor is preferably cooled in one or more coolers, preferably with generation of steam at one or more temperature levels.

Contaminants are preferably removed from the gas composition before it is supplied to the alkylene oxide absorber. Possible contaminants include acids, esters, aldehydes, acetals and organic halides. A preferred method of removing contaminants is quenching, preferably by contacting the gas composition with a cooled recirculating aqueous solution. Quenching is preferably carried out in the same vessel as the alkylene oxide absorber. A portion of the recirculating aqueous solution may be withdrawn as a bleed stream from the quench section, and any alkylene oxide in the bleed stream may be recovered by conventional methods. After quenching, the gas composition may be reheated before it is supplied to the alkylene oxide absorber, preferably by heat integration with the hot gas composition emerging from the alkylene oxide reactor.

The alkylene oxide absorber preferably comprises a column of vertically stacked trays or a packed column. The trays or the packed column provide a surface area for the absorbent and gas composition to come into contact, facilitating mass transfer between the two phases. Additionally, trays provide considerable liquid volume in which the liquid phase reaction can occur. In the embodiment wherein the alkylene oxide absorber comprises a series of vertically stacked trays, gases can pass upwards through the trays and liquid can flow downwards from tray to tray. Preferably the column comprises at least 20 trays, more preferably at least 30 trays. Preferably the column comprises less than 70 trays. More trays increase the absorption ability of the column, but adding additional trays increases expense. In the embodiment wherein the alkylene oxide absorber comprises a packed column, conventional packing such as structured packing, random packing and catalytic distillation internals may be used.

The gas composition from the oxidation step (a) is preferably supplied at the bottom of the alkylene oxide absorber. If the alkylene oxide absorber comprises a column of vertically stacked trays, the gas composition is preferably supplied below the bottom tray in the column. If the alkylene oxide absorber comprises a packed column, the gas composition is preferably supplied below the packing material.

Lean absorbent is supplied to the alkylene oxide absorber and contacted with the gas composition in the alkylene oxide absorber and fat absorbent (comprising components absorbed from the gas composition and comprising alkylene glycol) is withdrawn from the alkylene oxide absorber. In one embodiment, the lean absorbent is supplied at the top of the alkylene oxide absorber. If the alkylene oxide absorber comprises a column of vertically stacked trays, the lean absorbent is preferably supplied to the uppermost tray in the absorption column. If the alkylene oxide absorber comprises a packed column, the lean absorbent is preferably supplied above the packing material. In another embodiment, the lean absorbent is supplied such that there are trays or packing above the point at which the lean absorbent is supplied to the alkylene oxide absorber. In this embodiment, cold water or additional lean absorbent that has been cooled can be supplied at the top of the alkylene oxide absorber to absorb alkylene oxide or contaminants in the top of the alkylene oxide absorber.

The lean absorbent preferably comprises at least 20 wt % water. More preferably, the lean absorbent comprises at least 50 wt % water, most preferably at least 70 wt % water.

The gas composition is contacted with lean absorbent in the alkylene oxide absorber in the presence of one or more catalysts that promote hydrolysis. The presence of a hydrolysis catalyst means that the alkylene oxide absorber acts as both an absorber, absorbing alkylene oxide from the gas composition, and as a reactor, converting alkylene oxide to alkylene glycol. The fat absorbent resulting from step (b) therefore comprises alkylene glycol. Carrying out both the absorption and the hydrolysis in the alkylene oxide absorber has the advantage of reducing the requirement for additional reaction vessels wherein hydrolysis would occur, and can therefore lead to a reduction in capital costs.

The one or more catalysts that promote hydrolysis may be homogeneous, so that the lean absorbent comprises the one or more catalysts. Homogeneous catalysts that are known to promote hydrolysis include basic alkali metal salts such as potassium carbonate, potassium hydroxide and potassium bicarbonate; alkali metal metalates such as potassium molybdate; or acidic catalysts such as sulphuric acid. Alternatively, the one or more catalysts that promote hydrolysis may be heterogeneous and the heterogeneous catalyst(s) are contained in vertically stacked trays or in the packing of a packed column. Heterogeneous catalysts that promote hydrolysis include metalates immobilised on solid supports, for example molybdates, vanadates or tungstates immobilised on ion exchange resins containing quaternary ammonium or quaternary phosphonium groups; basic anions such as bicarbonate ions immobilised on solid supports, for example bicarbonate immobilised on ion exchange resins containing quaternary ammonium or quaternary phosphonium groups; or acidic catalysts such as zeolites, acidic clays or acidic ion exchange resins.

In an embodiment of the invention, the gas composition is contacted with lean absorbent in the alkylene oxide absorber in the presence of one or more catalysts that promote carboxylation. The presence of both a hydrolysis catalyst and a carboxylation catalyst means that the alkylene oxide absorber acts as both an absorber, absorbing alkylene oxide from the gas composition, and as a reactor, converting alkylene oxide to alkylene glycol via alkylene carbonate. The fat absorbent resulting from step (b) therefore comprises alkylene glycol. This embodiment has the advantages of ensuring high selectivity.

In this embodiment of the invention, the one or more catalysts that promote carboxylation may be homogeneous, so that the lean absorbent comprises the one or more catalysts. Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Alternatively, the one or more catalysts that promote carboxylation may be heterogeneous and the heterogeneous catalyst(s) are contained in vertically stacked trays or in the packing of a packed column. Heterogeneous catalysts that promote carboxylation include quaternary ammonium and quaternary phosphonium halides immobilized on silica, quaternary ammonium and quaternary phosphonium halides bound to insoluble polystyrene beads, and metal salts such as zinc salts immobilised on solid supports containing quaternary ammonium or quaternary phosphonium groups, such as ion exchange resins containing quaternary ammonium or quaternary phosphonium groups.

In an embodiment of the invention, the gas composition is contacted with lean absorbent in the alkylene oxide absorber in the presence of a metal carbonate, preferably an alkali metal carbonate. The metal carbonate is likely to act as a hydrolysis catalyst. However, the metal carbonate also acts to promote absorption of carbon dioxide in the alkylene oxide absorber so that the fat absorbent leaving step (b) comprises carbon dioxide. Preferably the lean absorbent comprises further additives such as metal vanadates and metal borates that promote further absorption of carbon dioxide in the absorber.

The alkylene oxide absorber functions as both an absorber, absorbing alkylene oxide from the gas composition from step (a), and as a reactor such that conversion of alkylene oxide to alkylene glycol occurs in step (b), such that the fat absorbent resulting from step (b) comprises alkylene glycol. If significant conversion (e.g. at least 50% conversion) of alkylene oxide to alkylene glycol occurs in the absorber, then step (c) is not necessary. It is preferred that conversion of alkylene oxide to alkylene glycol is maximised in step (b) such that the reactor vessels in step (c) can be made smaller, or that step (c) can be eliminated entirely.

The pressure in the alkylene oxide absorber is from 1 to 4 MPa, preferably from 2 to 3 MPa. The preferred pressure is a compromise between lower pressures that require less expensive equipment (e.g. equipment having thinner walls) and higher pressures that increase absorption and reduce the volumetric flow of the gas, thereby reducing the size of equipment and piping.

Gases that are not absorbed in the alkylene oxide absorber are preferably recycled to the alkylene oxide reactor. In a conventional process, gases are that are not absorbed in the absorber are typically supplied to a carbon dioxide absorption column wherein carbon dioxide is at least partially absorbed by a recirculating absorbent stream. In the embodiment of the present invention where the gas composition is contacted with lean absorbent in the alkylene oxide absorber in the presence of a metal carbonate, carbon dioxide is absorbed into the fat absorbent and it may not be necessary to supply the gases that are not absorbed in the alkylene oxide absorber to a carbon dioxide absorption column (they can be recycled directly to the alkylene oxide reactor), or it may be possible to use a smaller carbon dioxide absorption column.

Fat absorbent is withdrawn from the alkylene oxide absorber, preferably by withdrawing liquid from the bottom of the alkylene oxide absorber. Optionally, the fat absorbent is supplied to one or more reactor vessels, wherein further reaction of alkylene oxide to alkylene glycol occurs. As explained above, the need for these reactor vessels is determined by the amount of conversion that occurs in the alkylene oxide absorber. In a most preferred embodiment, sufficient conversion occurs in the alkylene oxide absorber such that no further reaction vessels are required. (For the purposes of this description, the "alkylene oxide absorber" encompasses the absorption vessel, e.g. a column, and piping that connects the absorption vessel to the next reaction vessel in the process.) In another embodiment, the one or more reaction vessels essentially function as finishing reactors, i.e. more than 50% conversion occurs in step (b) and further conversion occurs in step (c). The one or more reaction vessels in step (c) may be hydrolysis reactors (achieving hydrolysis via catalytic methods or thermal methods) or may be both carboxylation and hydrolysis reactors (converting alkylene oxide to alkylene glycol via alkylene carbonate).

The fat absorbent comprising alkylene glycol that results from step (b) or step (c) is optionally supplied to a flash vessel wherein light ends are removed. Light ends are gases such as the alkene, and also ballast gases such as methane, that are present in the gas composition resulting from (a) and are absorbed into the absorbent in step (b). The light ends are preferably recirculated to the alkylene oxide reactor. Recirculating the light ends to the alkylene oxide reactor increases the efficiency of the process because light ends, comprising alkene, are recovered. The flash can be at pressure from 0.01 to 2 MPa, preferably from 0.1 to 1 MPa, most preferably from 0.1 to 0.5 MPa.

In step (d), the fat absorbent is contacted with a lean solvent, thereby extracting alkylene glycol from the fat absorbent and producing fat solvent. The lean solvent is preferably an alcohol (a compound having one hydroxyl group), e.g. benzylalcohol or phenyl glycol, or a polyol (a compound having multiple hydroxyl groups). Preferably the polyol has a molecular weight of greater than 250. Preferred polyols are prepared from glycerol and propylene oxide and/or ethylene oxide. Standard extraction equipment may be used, e.g. mixer settlers in combination with emulsion breakers such as plate packages or coalescence elements.

After the fat absorbent has been contacted with a lean solvent in step (d), it is preferably recirculated to the alkylene oxide absorber as lean absorbent. In the embodiment of the present invention where the gas composition is contacted with lean absorbent in the alkylene oxide absorber in the presence of a metal carbonate, carbon dioxide is present in the fat absorbent and preferably carbon dioxide is removed before the fat absorbent is recirculated to the alkylene oxide absorber as lean absorbent. Preferably the carbon dioxide is removed by passing the fat absorbent to a carbon dioxide stripper. Carbon dioxide is removed over the top, and lean absorbent is withdrawn from the bottom and recirculated to the alkylene oxide absorber.

The alkylene glycol is recovered from the fat solvent, thereby producing lean solvent. This is preferably achieved by passing the fat solvent to a water removal column (wherein water is removed over the top and glycol-containing solvent is removed from the bottom) and then to a distillation column. If the boiling point of the lean solvent is higher than the boiling point of glycols, then the crude glycol is removed over the top and lean solvent is removed from the bottom. If the boiling point of the lean solvent is lower than the boiling point of the glycols, then the lean solvent is removed over the top and the glycols are removed from the bottom. The lean solvent is recycled to step (d).

The alkylene glycol that is recovered from the fat solvent is still in a crude form and will comprise a mixture of alkylene glycols (monoalkylene glycol, dialkylene glycol and higher glycols) and water. The crude alkylene glycol is preferably supplied to a dehydrator column. The dehydrator is preferably one or more columns, including at least one vacuum column, preferably operating at a pressure of less than 0.05 MPa, more preferably less than 0.025 MPa and most preferably about 0.0125 MPa. The water that is removed in the dehydrator column is preferably recombined with the portion of lean absorbent that is supplied to the alkylene oxide absorber. The alkylene glycol is preferably also supplied to conventional distillation apparatus to separate the monoalkylene glycol, dialkylene glycol, trialkylene glycol and higher glycols.

If one or more homogeneous catalysts are used in either step (b) or step (c), they will be present in the fat absorbent and are preferably recycled as part of the lean absorbent.

FIG. 1 shows an embodiment of the process of the invention. Ethylene, oxygen, methane and inhibitor gas (e.g. monochloroethane) are supplied to the recycle gas at (1). In the ethylene oxide reactor (2), the ethylene and oxygen react, providing a gas composition comprising ethylene, oxygen, ethylene oxide and carbon dioxide, which is supplied to a quench section (3) below the ethylene oxide absorber (4). (NB The number of trays shown for the absorber is not indicative of the number of trays likely to be present in the absorber, but merely shows that the absorber contains a series of vertically stacked trays). Lean absorbent comprising potassium carbonate is supplied (5) to the absorber (4) at the top of the absorber, into the uppermost tray. In the absorber, ethylene oxide and carbon dioxide are absorbed into the absorbent. The ethylene oxide reacts with water in the presence of the potassium carbonate hydrolysis catalyst to provide monoethylene glycol. Gases not absorbed in the absorber (4) are recycled to the ethylene oxide reactor (2). Fat absorbent comprising monoethylene glycol, carbon dioxide and potassium carbonate is withdrawn from the absorber (4) and supplied to a flash vessel (6). Light ends are removed and are recycled to the ethylene oxide absorber (2). The fat absorbent is then supplied from the flash vessel (6) to an extractor system (7) that consists of one or more mixer settlers. Lean solvent is supplied (8) to the extractor system (7). The lean solvent contacts the fat absorbent in the extractor system (7) and extracts ethylene glycols from the fat absorbent. Fat solvent, containing monoethylene glycol and higher glycols, is withdrawn (9) from the extractor vessel (7), supplied to the water removal column (10) and then supplied to the distillation column (11). Monoethylene glycol, diethylene glycol, triethylene glycol and higher glycols are withdrawn (12) from the distillation column (11) and are subjected to further purification. Lean solvent is withdrawn from the distillation column (11) and recirculated (8) to the extractor system (7). Lean absorbent is withdrawn (13) from the extractor vessel (7) and supplied to carbon dioxide stripper (14). Carbon dioxide is removed (15) from the stripper and lean absorbent is recirculated (5) to the absorber (4).

Figure 2:
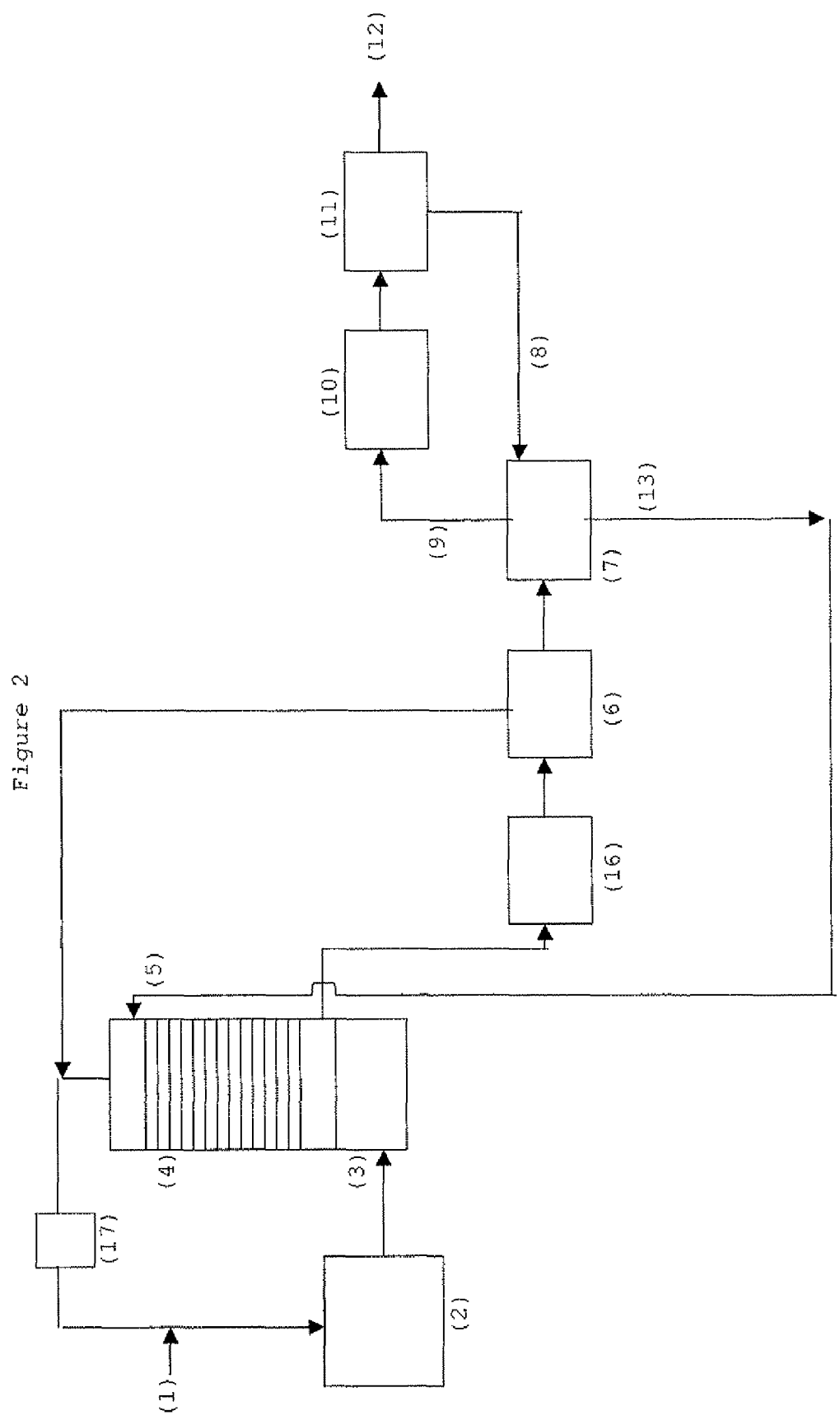
FIG. 2 is a schematic diagram showing a process according to a second embodiment of the invention.

FIG. 2 shows a further embodiment of the process of the invention. All the elements are the same as for FIG. 1 except that there is an additional reactor vessel (16), which functions as a finishing reactor, there is a carbon dioxide absorber (17) in the recycle to the ethylene oxide reactor (2), and the lean absorbent does not pass through a carbon dioxide stripper. Fat absorbent is withdrawn from the absorber (4) and supplied to the finishing reactor (16). Conversion of ethylene oxide to monoethylene glycol has occurred in the absorber (4), but further conversion of ethylene oxide to monoethylene glycol occurs in the finishing reactor (16). Fat absorbent from the finishing reactor (16) is supplied to the flash vessel (6). The gases from the flash vessel (6) and the unreacted gases from the ethylene oxide absorber (4) are subjected to carbon dioxide absorption in the carbon dioxide absorber (17) before they are supplied to the ethylene oxide reactor (2).

What is claimed is:

1. A process for the preparation of an alkylene glycol from an alkene comprising steps of:
    (a) reacting the alkene with oxygen in the presence of a catalyst in a reactor to produce a gas composition comprising alkylene oxide, alkene, oxygen, carbon dioxide and water vapour;
    (b) supplying the gas composition from (a) to an alkylene oxide absorber, supplying lean absorbent to the alkylene oxide absorber, contacting the gas composition with lean absorbent in the absorber in the presence of one or more catalysts that promote hydrolysis and withdrawing fat absorbent from the absorber;
    (c) optionally supplying the fat absorbent to one or more reactor vessels; wherein conversion of alkylene oxide to alkylene glycol occurs in step (b) and optionally in step (c), such that the fat absorbent resulting from step (b) or step (c) comprises alkylene glycol; and further comprising steps of:
    (d) contacting the fat absorbent from step (b) or step (c) with a lean solvent, thereby extracting alkylene glycol from the fat absorbent and producing fat solvent; and
    (e) recovering alkylene glycol from the fat solvent, thereby producing lean solvent, and recycling the lean solvent to step (d).

2. A process according to claim 1, wherein contaminants are removed from the gas composition before it is supplied to the alkylene oxide absorber by contacting the gas composition with a cooled recirculating aqueous solution.

3. A process according to claim 1, wherein the gas composition is contacted with lean absorbent in the alkylene oxide absorber in the presence of one or more catalysts that promote carboxylation.

4. A process according to claim 1, wherein the gas composition is contacted with lean absorbent in the alkylene oxide absorber in the presence of a metal carbonate.

5. A process according to claim 1, wherein fat absorbent comprising alkylene glycol that results from step (b) or step (c) is supplied to a flash vessel wherein light ends are removed, before step (d).

6. A process according to claim 1, wherein the lean solvent is an alcohol or a polyol.

7. A process according to claim 1, wherein after the fat absorbent has been contacted with a lean solvent in step (d), it is recirculated to the alkylene oxide absorber as lean absorbent.

8. A process according to claim 1, wherein the alkylene glycol is recovered from the fat solvent by passing the fat solvent to a water removal column and then to a distillation column.

9. A process according to claim 1, wherein the alkylene glycol recovered in step (e) is supplied to a dehydrator column and to distillation apparatus.

* * * * *